US 8,632,487 B2
Jan. 21, 2014

(12) United States Patent
Günther et al.

(10) Patent No.: US 8,632,487 B2
(45) Date of Patent: Jan. 21, 2014

(54) DEVICE FOR CONTROLLING A SYSTEM FOR TRANSPORTING BLOOD, AND METHOD FOR TRANSPORTING BLOOD IN A BLOOD LINE OF AN EXTRACORPOREAL BLOOD CIRCUIT OF AN EXTRACORPOREAL BLOOD TREATMENT DEVICE

(75) Inventors: Götz Günther, Oberursel (DE); Michael Herrenbauer, Neu-Anspach (DE); Martin Lauer, St. Wendel (DE); Ralf Müller, Bad Homburg (DE)

(73) Assignee: Fresenius Medical Care Deutchland GmbH, Bad Homburg (DE)

( * ) Notice: Subject to any disclaimer, the term of this patent is extended or adjusted under 35 U.S.C. 154(b) by 901 days.

(21) Appl. No.: 12/602,813

(22) PCT Filed: May 31, 2008

(86) PCT No.: PCT/EP2008/004354
§ 371 (c)(1),
(2), (4) Date: Dec. 3, 2009

(87) PCT Pub. No.: WO2008/148506
PCT Pub. Date: Dec. 11, 2008

(65) Prior Publication Data
US 2010/0179467 A1  Jul. 15, 2010

(30) Foreign Application Priority Data

Jun. 4, 2007 (DE) .......................... 10 2007 026 010

(51) Int. Cl.
*A61M 37/00* (2006.01)
(52) U.S. Cl.
USPC .......................... 604/6.15; 604/4.01; 604/6.11
(58) Field of Classification Search
USPC .............................. 604/4.01–6.16; 422/44–48
See application file for complete search history.

(56) References Cited

U.S. PATENT DOCUMENTS 4,828,543 A    5/1989   Weiss et al.
5,178,603 A    1/1993   Prince
(Continued)

FOREIGN PATENT DOCUMENTS

DE    10 2005 001 779 A1    9/2006
EP    0405094 A2    1/1991
EP    0472480 B1    2/1992
JP    62-233166    10/1987
JP    05-168704    7/1993
(Continued)

OTHER PUBLICATIONS

International Search Report, PCT/EP2008/004354, mailed Mar. 11, 2009.

*Primary Examiner* — Philip R Wiest
(74) *Attorney, Agent, or Firm* — Kenyon and Kenyon LLP

(57) ABSTRACT

The present invention relates to a device for controlling a system for transporting blood, and a method for transporting blood in a blood line of an extracorporeal blood circuit of an extracorporeal blood treatment system. The present invention also relates to an extracorporeal blood treatment device comprising such a system for transporting blood. The method and device according to the present invention are based on the fact that a defined threshold value for the pressure in the blood line should not be exceeded. The system for transporting blood is controlled in such a way the blood in the blood line is transported in a pre-determined volume flow as long as the pressure in the blood line is below the pre-determined threshold value. When the pressure in the blood line reaches the pre-defined threshold value, however, the system for transporting blood is controlled such that a pressure value corresponding to the threshold value is set when the blood is transported in the blood line. As a result, when the threshold value for the pressure is reached, a regulation of the volume flow is replaced by a regulation of the pressure in the blood line.

14 Claims, 7 Drawing Sheets

(56) References Cited

U.S. PATENT DOCUMENTS

| | | | |
|---|---|---|---|
| 5,227,049 A | 7/1993 | Chevallet et al. | |
| 2001/0021817 A1 | 9/2001 | Brugger et al. | |
| 2002/0041825 A1* | 4/2002 | Scheunert et al. | 422/44 |
| 2003/0152482 A1* | 8/2003 | O'Mahony et al. | 422/44 |
| 2005/0230313 A1* | 10/2005 | O'Mahony et al. | 210/645 |

FOREIGN PATENT DOCUMENTS

| | | |
|---|---|---|
| JP | 05-509022 | 12/1993 |
| JP | 2005-512736 | 5/2005 |
| WO | 92/02264 | 2/1992 |
| WO | 03/055542 | 7/2003 |
| WO | 03/072942 A1 | 9/2003 |

\* cited by examiner

DEVICE FOR CONTROLLING A SYSTEM FOR TRANSPORTING BLOOD, AND METHOD FOR TRANSPORTING BLOOD IN A BLOOD LINE OF AN EXTRACORPOREAL BLOOD CIRCUIT OF AN EXTRACORPOREAL BLOOD TREATMENT DEVICE

CROSS REFERENCE TO RELATED APPLICATIONS

This is a 371 national phase application of PCT/EP2008/004354 filed May 31, 2008, claiming priority to German Patent Application No. 10 2007026 010.7 filed Jun. 4, 2007.

FIELD OF INVENTION

The present invention relates to an apparatus for controlling a device for transporting blood in a blood conduit of an extracorporeal blood circuit of an extracorporeal blood treatment apparatus, wherein the extracorporeal blood treatment apparatus can be a blood treatment apparatus, in particular a dialysis apparatus, which can be operated in a single-needle mode or a two-needle mode. Furthermore, the present invention relates to an extracorporeal blood treatment apparatus, with such a device for transporting blood in a blood conduit of the extracorporeal blood circuit of the blood treatment apparatus. The present invention furthermore relates to a method for transporting blood in a blood conduit of an extracorporeal blood circuit of an extracorporeal blood treatment apparatus, wherein the blood treatment can take place in a single-needle mode or a two-needle mode.

BACKGROUND OF THE INVENTION

Blood treatment apparatuses with a blood treatment unit through which a patient's blood flows are generally known. These include for example the familiar hemodialysis, hemofiltration or hemodiafiltration apparatuses. These known blood treatment apparatuses can be operated in a single-needle mode or a two-needle mode.

The blood treatment apparatuses for both single-needle and two-needle operation have an extracorporeal blood circuit with an arterial blood conduit that leads to the blood treatment unit, and a venous blood conduit that leads away from the blood treatment unit.

In the case of the two-needle technique, the blood is taken from one of the patient's blood vessels via an arterial needle; it is then directed into the blood treatment unit of the blood treatment apparatus, and is returned via a venous needle into one of the patient's blood vessels. Replaceable hose systems with a blood supply line and a blood return line, to which the two needles are connected, are used for taking and returning the blood. These single-use hose systems are also referred to as "disposables".

In the case of the single-needle technique, the blood is extracted and returned via a single needle, to which both the arterial and the venous blood conduits are connected. The blood that is taken from the patient is stored in a reservoir during an arterial phase, in order to be led out of the reservoir into the patient's blood circuit in a venous phase, through the same needle.

A blood treatment apparatus for single-needle operation is known from EP-A-0 472 480 B1. In the case of one embodiment of this known blood treatment device, two blood expansion chambers are provided for the temporary storage of blood, which are arranged upstream and downstream of the blood treatment unit. The blood treatment unit has a control device that keeps the pressure in the expansion chambers essentially constant. Level sensors are provided, to detect the fluid level in the expansion chambers.

The document DE 10 2005 001 779 A1 describes a set for a disposable, for operating a blood treatment apparatus in a single-needle or a two-needle mode. Besides the blood supply and blood return conduit for connection to a blood treatment unit, the disposable includes an expansion unit, which for single-needle operation can be coupled to the air separation unit in order to increase the volume. During single-needle operation, in the arterial phase blood is transported through the blood supply conduit into the blood treatment unit and out of the blood treatment unit into the air separation and expansion unit, wherein the blood supply to the patient is interrupted. In the course of this, a given pressure is built up in the air separation and expansion unit, this pressure being monitored with a pressure measurement unit. With a compressed air unit, by operating an air pump that is connected between a tank and the expansion unit, a given pressure can be set in the expansion and air separation unit. It is also proposed that the blood volume in the expansion and air separation unit be calculated with the aid of the measured values from three pressure sensors and the known system volumes. It is furthermore proposed that the air pump be used to control the pressure during the venous phase, so that the transportation rate of the blood can be optimally adapted.

For the proper operation of blood treatment apparatuses in both single-needle and two-needle operation, it is important that blood is supplied back to the patient at a predetermined volume flow rate.

SUMMARY OF THE INVENTION

One object of the present invention is to provide an apparatus for controlling a device for transporting blood in a blood conduit of an extracorporeal blood circuit of an extracorporeal blood treatment apparatus, which permits optimum control of the blood flow whilst avoiding the occurrence of pressure peaks.

Furthermore, another object of the present invention is to create an extracorporeal blood treatment apparatus with such a control device, in which there is optimum control of the blood flow whilst avoiding the occurrence of pressure peaks.

A further object of the present invention is to define a method with which the blood can be transported in a blood conduit of an extracorporeal blood circuit of an extracorporeal blood treatment apparatus whilst avoiding the occurrence of pressure peaks.

The method according to the present invention and the apparatus according to the present invention are based on the fact that a particular limit value is specified for the pressure in the blood conduit, which must not be exceeded. Here, the limit value for the maximum pressure in the blood conduit can be dimensioned such that the limit value lies above the pressure at which the alarm devices respond, which are generally provided in the familiar extracorporeal blood treatment apparatuses. In general, the limit value adopted for the pressure is not an absolute value for the pressure, but a relative value related to the ambient pressure. A change in the ambient pressure thus does not lead to a change in the limit value relative to this pressure. In principle, however, the limit value can also be an absolute value for the pressure.

In the case of the blood treatment apparatus, in principle two limit value windows can be set for the pressure, wherein one limit value window relates to the overpressure in the venous blood conduit with which the blood is supplied back to the patient, and the other limit value window relates to the low pressure in the arterial blood conduit with which blood is taken from the patient. By monitoring both these limit value windows, it is ensured that the blood flow in the extracorporeal blood treatment apparatus is in order.

The apparatus according to the present invention and the method according to the present invention are furthermore based on the fact that the device for transporting blood is actuated in such a way that the blood in the blood conduit continues to be transported at a given volume flow rate as long as the pressure in the blood conduit lies below the specified limit value. However, once the pressure in the blood conduit reaches the specified limit value, the device for transporting blood is actuated in such a way that when the blood is transported in the blood conduit, a pressure is achieved that conforms to the limit value. Consequently, when the limit value for the pressure is reached, the system switches over from control of the volume flow rate to control of the pressure in the blood conduit, without the device for transporting blood being stopped immediately.

As long as the pressure in the blood conduit does not reach the specified limit value, neither short-term changes in flow resistance (e.g. as a result of changes in the needle position, for example when the patient moves his arm) nor slow changes in the flow resistance (e.g. in the case of a rise in the hematocrit) lead to any changes in the volume flow rate of the blood during the blood treatment.

Since the pressure with which blood is supplied to the patient (overpressure) or the pressure with which blood is taken from the patient (low pressure) is limited to a given value, unwanted pressure peaks in the extracorporeal blood circuit, which could damage the patient's vascular system (shunt), are avoided.

The control device according to the present invention is a fundamental constituent part of an extracorporeal blood treatment apparatus, which has a device for transporting blood in a blood conduit of an extracorporeal blood circuit. Here, the control device according to the present invention can make use of the components that generally already exist in the familiar blood treatment apparatuses.

The extracorporeal blood treatment apparatus with the control device according to the present invention can be a blood treatment apparatus for operation with two patient connection points (two-needle operation), in which the arterial blood conduit has an arterial patient connection point and the venous blood conduit has a venous patient connection point. In the case of such a blood treatment apparatus, the device for transporting blood is a blood pump that is arranged in the extracorporeal blood circuit, in particular in the arterial blood conduit.

In the case of an extracorporeal blood treatment apparatus for two-needle operation, a value can be specified for the amount of maximum pressure in the venous blood conduit and/or the arterial blood conduit, in order to ensure that blood is not supplied to the patient at too great an overpressure, and/or taken from the patient at too great a low pressure.

The decisive advantages of the control device according to the present invention and of the method according to the present invention are also shown in the case of an extracorporeal blood treatment apparatus for operation with one patient connection point (single-needle operation), in which the arterial blood conduit and the venous blood conduit have a common patient connection point.

The blood treatment apparatus for single-needle operation has a means for collecting blood arranged in the venous blood conduit of the extracorporeal blood circuit, which have a given volume. The means for collecting blood can however also be arranged in the arterial conduit. In the case of the blood treatment apparatus for single-needle operation, the device for transporting blood is a device for producing a specified pressure in the means for collecting blood, so that blood that has collected in the means for collecting blood is displaced out of the means for collecting blood.

The device for producing a given pressure in the means for collecting blood can be of varying designs. For example, the device for producing a given pressure can be a compressor, with which an overpressure can be produced.

In the case of the extracorporeal blood treatment apparatus for single-needle operation, during an arterial phase blood is transported to the means for collecting blood, which contain a closed volume, and during a venous phase a given pressure is built up in the means for collecting blood, so that blood that has collected in the means for collecting blood is displaced. In the course of this, there is continual switching between the arterial and the venous phases.

In the case of the extracorporeal blood treatment apparatus for single-needle operation, the user can specify a limit value for the pressure in the venous blood conduit, i.e. the maximum return pressure, and a particular volume flow rate, i.e. a reference volume flow rate. The maximum return pressure is preferably a relative pressure in relation to the ambient pressure. It can however in principle also be an absolute pressure.

In contrast to a method in which a given reference pressure in the closed volume of the means for collecting blood is set, which is to be maintained during the venous phase, in the case of the control device or method according to the present invention, the pressure in the closed volume of the means for collecting blood is controlled such that the specified volume flow rate in the venous blood conduit results. For this, the reference volume flow rate specified by the user is compared with the measured or calculated actual volume flow rate. Consequently, the blood in the venous blood conduit flows at the reference volume flow rate that is specified by the user, as long as the return pressure does not exceed the maximum pressure specified by the user.

If the flow resistance changes briefly, e.g. in the event of a change in the position of the patient connection point, the return pressure can be increased up to the specified maximum pressure, so that the effective volume flow rate is kept constant, as long as the maximum return pressure is not exceeded. Slow changes in flow resistance too, for example in the case of a rise in the hematocrit, lead to an increase in the return pressure up to the maximum return pressure, so that the volume flow is kept constant, as long as the maximum return pressure is not exceeded.

A preferred embodiment of the present invention provides that regulation of the volume flow rate takes place with a first control circuit which has means for calculating a reference pressure for the closed volume of the means for collecting blood, which is dimensioned such that the specified volume flow rate is achieved in the venous blood conduit, and with a second control circuit which controls the device for producing a given pressure in the means for collecting blood in such a way that the calculated reference pressure is also achieved in the closed volume of the means for collecting blood.

A further particularly preferred embodiment provides that in the case of the extracorporeal blood treatment apparatus for single-needle operation, air from means for storing air is transported to the means for collecting blood with means for compressing air, which are arranged in a connecting path between the means for collecting blood and the means for storing air. In the case of this embodiment, the means for collecting blood and the means for storing air, together with the connecting path, form a closed volume, into which in principle no air can enter and from which no air can escape.

BRIEF DESCRIPTION OF THE DRAWINGS

In the following, various design examples of the present invention are explained in detail, with reference to the drawings.

DETAILED DESCRIPTION OF THE DRAWINGS

The control device according to the present invention can be used for an extracorporeal blood treatment apparatus for both two-needle operation and single-needle operation. First of all, an extracorporeal blood treatment apparatus for two-needle operation with the control device is described.

Figure 1:
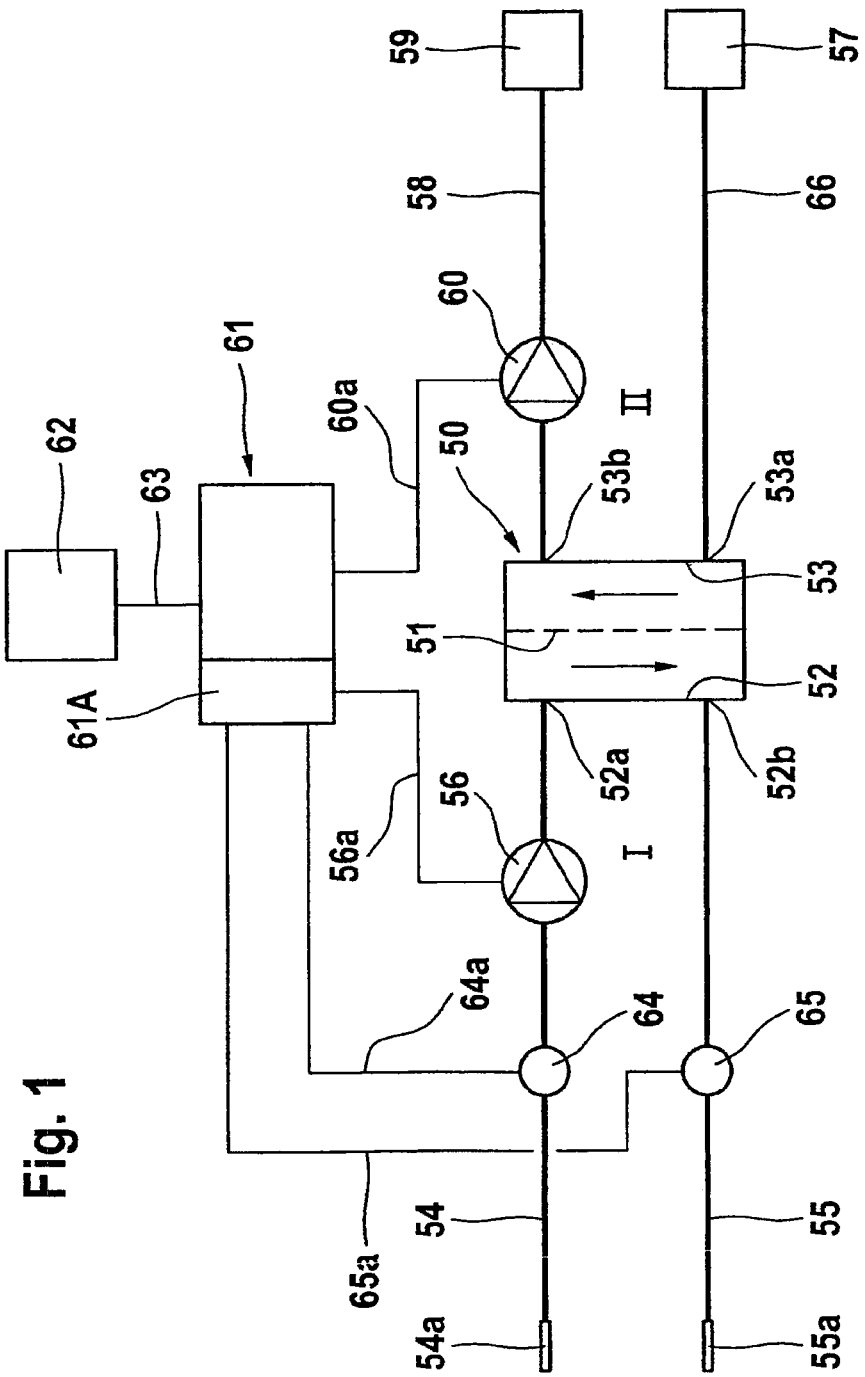
FIG. 1 shows a greatly simplified schematic representation of the essential components of an extracorporeal blood treatment apparatus for two-needle operation, which has an apparatus for controlling a device for transporting blood.

FIG. 1 shows a schematic representation of the essential components of an extracorporeal blood treatment apparatus for two-needle operation, in particular a hemodialysis apparatus. The arrangement has a dialyser 50 which is divided by a semi-permeable membrane 51 into a blood chamber 52 and a dialysis solution chamber 53.

An arterial blood conduit 54 with an arterial patient connection point 54a leads to an inlet 52a of the blood chamber 52, while a venous blood conduit 55 with a venous patient connection point 55a leads out from an outlet 52b of the blood chamber 52 of the dialyser 50. The patient connection points can be cannulas or needles, but they can also be connection elements with which the extracorporeal circuit is connected to existing patient connections such as catheters that have been placed. Arranged in the arterial blood conduit 54 is a blood pump 56, in particular a roll pump, which transports the blood in the extracorporeal blood circuit I. The arterial and venous blood conduits 54, 55 are designed as a disposable, which is inserted into the hemodialysis device. The dialyser 50 too, as well as the patient connection points 55a and 55b, are intended only for single use. In principle, however, a blood pump of a different design can also be used.

The dialysis solution circuit II comprises a dialysis solution supply conduit 66 which leads out from a dialysis solution source 57 and to an inlet 53a of the dialysis solution chamber 53, and a dialysis solution return conduit 58 which leads out from an outlet 53b of the dialysis solution chamber 53 of the dialyser 50 and to an outlet 59. Located in the dialysis solution return conduit 58 is a dialysis solution pump 60 for transporting the dialysis solution in the dialysis solution circuit II. The person skilled in the art will be familiar with the most varied types of pumps and balancing devices for the transportation of the dialysis solution, without the need for further detail on this at this point.

Furthermore, the hemodialysis apparatus has a central computing and control unit 61 and an input unit 62, which are connected to one another via a data line 63. The central control and computing unit 61, which is connected via a control line 56a to the blood pump 56 and via a control line 60a to the to the dialysis solution pump 60 actuates the blood pump and the dialysis solution pump such that both pumps are operated at a particular rotational speed.

Also provided is an arterial pressure sensor 64 for measuring the pressure in the arterial blood conduit 54 upstream of the blood pump 56, and a venous pressure sensor 65 for measuring the pressure in the venous blood conduit 55. The measured values of the two pressure sensors 64, 65 are transmitted, with data lines 64a, 65a, to the central control and computing unit 61.

The user can specify a particular volume flow rate for the blood flowing in the venous blood conduit 55. This volume flow rate can be entered with the input unit 62, for example using a keypad. It is however also possible for a particular value to be specified for the volume flow rate by the dialysis apparatus.

The user can furthermore also specify a maximum tolerable return pressure in the venous blood conduit 55, with which the blood is supplied back to the patient, and a maximum tolerable suction pressure—relating to the amount of low pressure—in the arterial blood conduit 54 upstream of the blood pump 56, with which the blood is taken from the patient. The user can enter the pressure values with the input unit 62. It is however also possible for the dialysis apparatus to specify values for the maximum tolerable return pressure or the minimum suction pressure. For preference, the return pressure or suction pressure is a relative pressure in relation to the ambient pressure, wherein the return pressure is stated with a positive value and the suction pressure is stated with a negative value here.

The hemodialysis apparatus has a device 61A for controlling the blood pump with which the blood is transported in the arterial and venous blood conduits. In the case of the present design example, the control device 61A is a constituent part of the central computing and control unit 61, but it can also form a separate unit. The control device 61A produces for the blood pump 56 a control signal with which the blood pump is actuated, with the rotational speed of the blood pump being set depending on the control signal.

The control device 61A compares the measured venous overpressure in the venous blood conduit 55 downstream of the blood pump 56, which preferably is a pressure that is relative to the ambient pressure, with the specified maximum tolerable return pressure, and compares the measured arterial low pressure in the arterial blood conduit 54 upstream of the blood pump 56, which likewise is preferably a pressure that is relative to the ambient pressure, with the specified minimum tolerable suction pressure.

Figure 2:
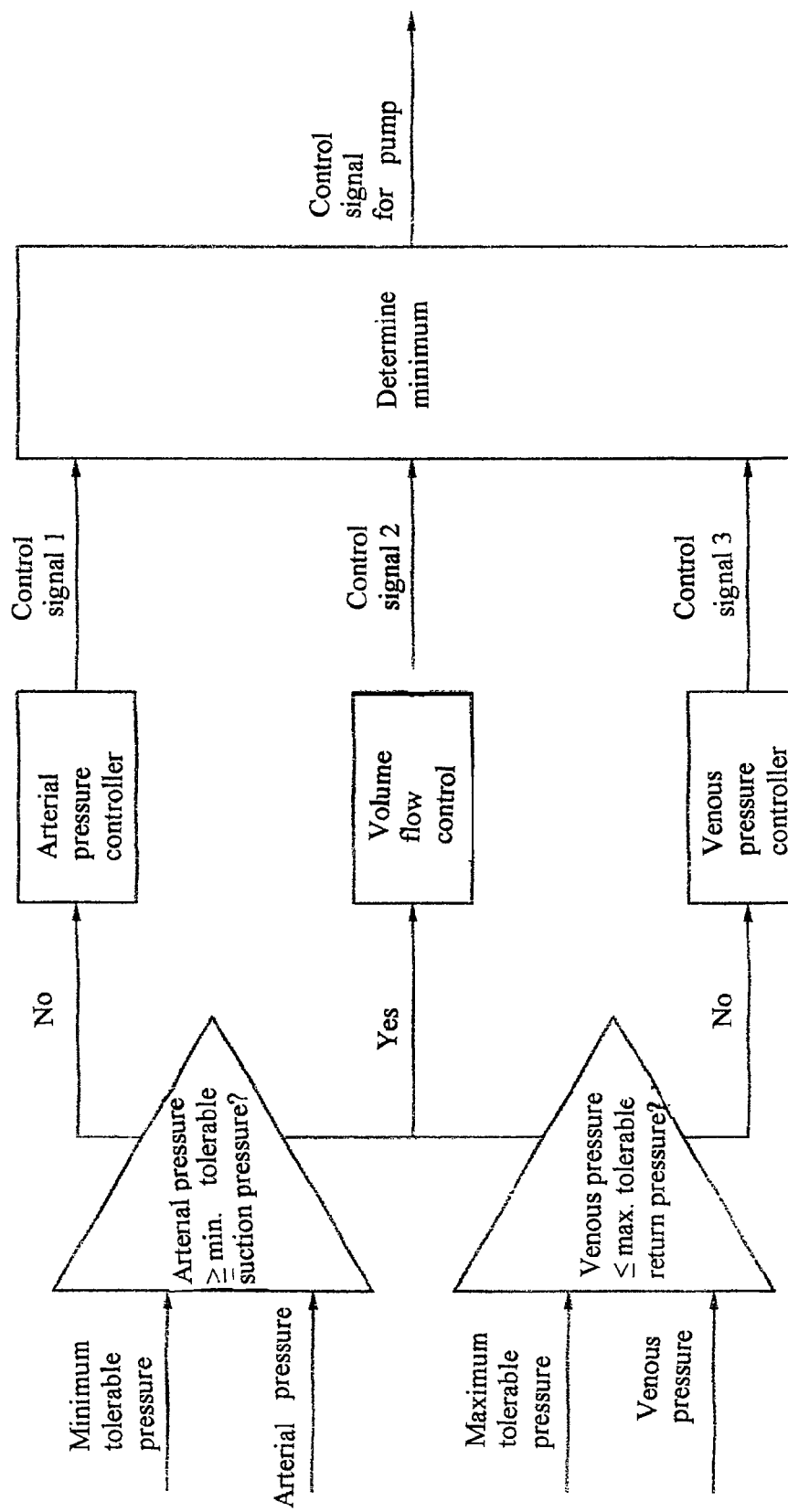
FIG. 2 shows a flow chart to illustrate the functional principle of the blood treatment apparatus of FIG. 1.

In the event that both the value of the venous return pressure is less than or equal to the maximum tolerable return pressure, and the value of the arterial suction pressure is greater than or equal to the minimum tolerable return pressure, the control device provides volume control with a control signal 2 for the blood pump (FIG. 2).

However, in the event that either the arterial pressure (low pressure) is less than the minimum tolerable suction pressure, or the venous pressure (overpressure) is greater than the maximum tolerable return pressure, the control device does not undertake volume control. In this case, arterial or venous pressure control is carried out.

For arterial pressure control, the control device 61A has an arterial pressure regulator, and for venous pressure control it has a venous pressure regulator. The arterial pressure regulator produces a control signal 1 for the blood pump, this signal being dimensioned such that the minimum tolerable suction pressure is achieved in the arterial blood conduit 54 upstream of the blood pump 56, i.e. the speed of the blood pump is regulated such that the pressure is kept constant, whilst the venous pressure regulator produces a control signal 3 which is dimensioned such that the maximum tolerable return pressure is achieved in the venous blood conduit 55, i.e. the speed of the blood pump is regulated such that the pressure in the venous conduit is kept constant. The control device 61A also has a device for selecting one of the three control signals 1, 2, 3 for operating the blood pump 56. In normal operation, volume flow control is effected with the control signal 2. Otherwise, the selection device selects from the two control signals 1 and 3 that control signal for the pump which corresponds to the "minimum" of the control signals 1 or 3; i.e. the blood pump is operated with a control signal such that neither of the two permitted limit values is breached.

So if the value of the arterial pressure is less than the minimum tolerable suction pressure, but the value of the venous pressure is still less than the maximum return pressure, the blood pump is actuated with the control signal 1 in such a way that blood is taken from the patient at the maximum tolerable suction pressure. In order to keep the suction pressure constant, the rotational speed of the blood pump is continually altered. If the value of the venous pressure is greater than the maximum tolerable return, but the value of the arterial pressure is still greater than the minimum suction pressure, the blood pump is actuated with the control signal 3 so that its speed is regulated depending on the venous pressure, so that the patient is supplied with blood at the maximum tolerable return pressure. If however both the arterial pressure is less than the minimum tolerable suction pressure and the venous pressure is greater than the maximum return pressure, the blood pump is operated such that neither the minimum suction pressure is undershot nor the maximum return pressure exceeded. The blood pump is thus operated such that either the minimum suction pressure or the maximum return pressure is achieved in the blood conduit, with the choice being made in such a way that neither of the two values lies outside the limit value window.

The control device according to the present invention can also be used in blood treatment apparatuses for single-needle use. If the blood treatment apparatus for single-needle use has two blood pumps, with which the blood is transported in the arterial and venous branch of the extracorporeal blood circuit, with the control device according to the present invention, both blood pumps can be actuated according to the method according to the present invention.

The advantages of the control device according to the present invention and of the control method according to the present invention are shown in particular in the case of a blood treatment apparatus for single-needle operation, in which the blood taken from the patient is collected in an arterial phase in means for collecting blood, and in a venous phase it is supplied from the means for collecting blood to the patient once more, in that the means for collecting blood are subjected to pressure in such a way that the blood that has collected in the means for collecting blood is displaced. Such a preferred embodiment of the blood treatment apparatus is described in detail below.

First of all the structure and functioning of the blood treatment apparatus for single-needle use as such is described, before the structure and functioning of the control device is described, which in the case of the present design example is a constituent part of the blood treatment apparatus.

Figure 3:
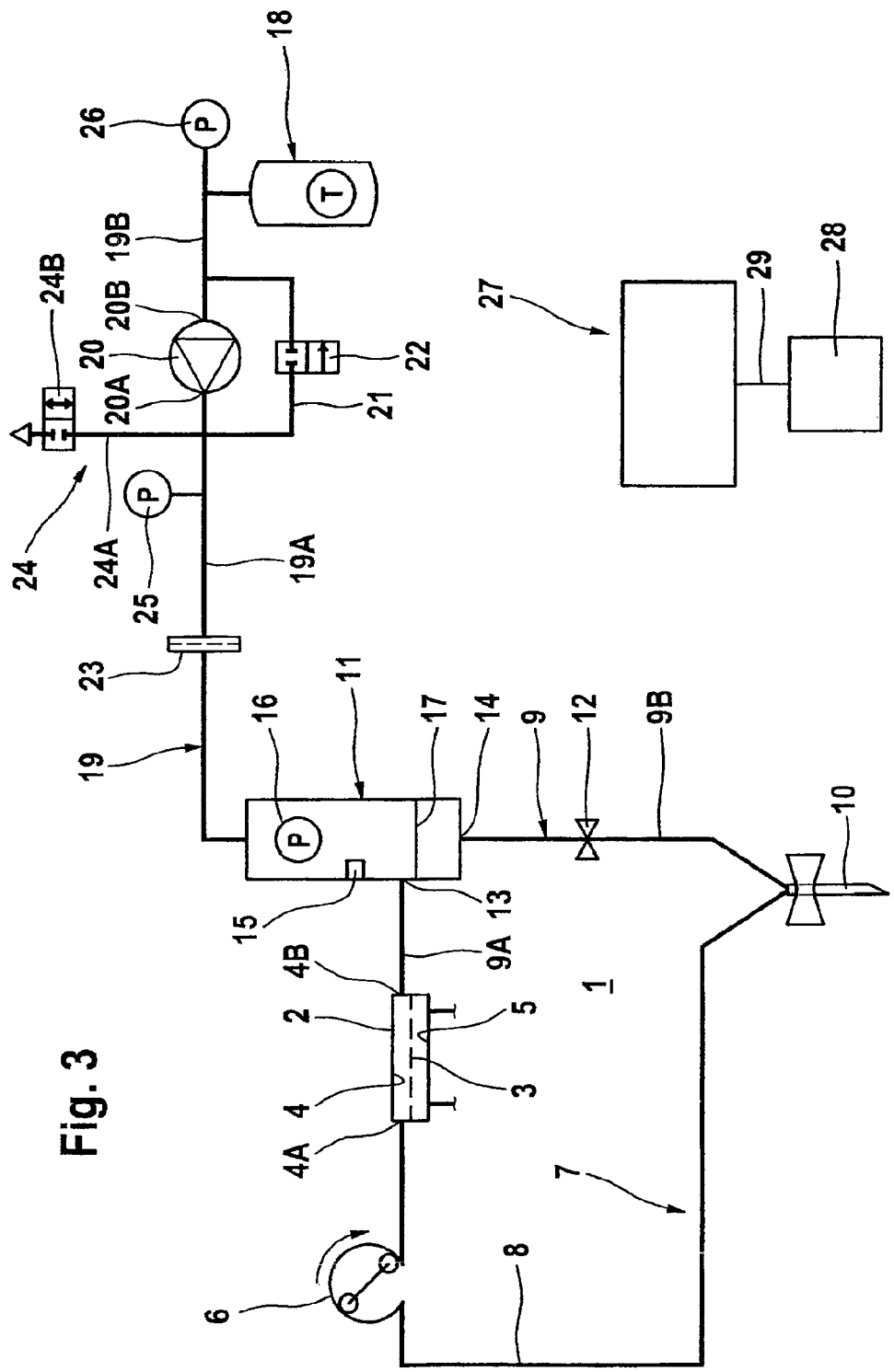
FIG. 3 shows a greatly simplified schematic representation of an extracorporeal blood treatment apparatus for single-needle operation with the control device according to the present invention.

FIG. 3 shows a schematic representation of the essential components of the blood treatment apparatus for single-needle use, in particular a dialysis apparatus.

During blood treatment, the dialysis apparatus has an extracorporeal blood circuit 1, which comprises a blood treatment unit 2, for example a dialyser designed as a disposable. The dialyser 2 is divided by a semi-permeable membrane 3 into a blood chamber 4 and a dialysis solution chamber 5.

In the extracorporeal blood circuit, the blood is transported by means of a blood pump 6, in particular a roll pump, but also by means of a pump of a different construction, which is part of the dialysis apparatus. The dialysis solution circuit, not shown in FIG. 3, can be designed as described with reference to FIG. 1.

Inserted into the dialysis apparatus is a hose set 7, which is also discarded after treatment. The disposable 7 has a blood supply conduit 8 which leads to the inlet 4A of the blood chamber 4 of the dialyser 2, and which is inserted into the roll pump 6 of the dialysis apparatus, and a blood return conduit 9 which leads out from the outlet 4B of the blood chamber. The blood supply conduit and the blood return conduit 8, 9 are connected to a common patient connection point 10 (cannula or needle). Arranged in the blood return conduit 9 are means 11 for collecting blood, which are designed as a container with a specified volume. In the following, the means for collecting blood are referred to as blood collection containers or blood reservoirs.

Downstream of the blood collection container 11, means 12 for interrupting the blood return flow, for example a venous hose clamp that can be actuated by the dialysis apparatus, are arranged on the blood return flow conduit 9.

The blood collection container 11 has an inlet 13, to which a first section 9A of the blood return conduit 9 leads, and also has an outlet 14, from which a second section 9B of the blood return 9 conduit leads out. For the detection of a particular fill level in the blood collection container 11, the dialysis apparatus has a fill level sensor 15 which detects if the fill level in the container reaches a predetermined value. Also provided is a pressure sensor 16, which measures the pressure in the blood collection container 11.

When the blood collection container 11 is filled with blood, a certain volume of air remains above the fluid level 17 in the blood reservoir. The blood collection container is in flow connection with means 18 for storing gas, in particular air, which are designed as a container with a closed volume. In the following, the means 18 for storing gas are referred to as air storage containers or air reservoirs.

In order for the blood reservoir and the air reservoir to be able to communicate with one another, a conduit 19 leads out from the top of the blood reservoir 11, and leads to the air reservoir 18. Arranged in the conduit 19 are means 20 for compressing gas, which for example can be designed as a conventional compressor. As long as the compressor is not operated, the compressor interrupts the flow connection between the blood reservoir and the air reservoir. When the compressor is operated, on the other hand, any air that is present in the air reservoir is conveyed into the blood reservoir. Since the air is compressed, a given pressure builds up in the blood reservoir.

The conduit 19 has two conduit sections 19A, 19B, of which the one conduit section 19A connects the blood reservoir to the pressure-side connection 20A of the compressor 20, and the other conduit section 19B connects the suction-side connection 20B of the compressor 20 to the air reservoir 18. These conduit sections 19A, 19B form a connection path for conveying gas from the blood reservoir into the air reservoir.

In order to be able to transport air from the blood reservoir into the air reservoir when the compressor is not in operation, a bypass conduit 21 is provided, which leads out from the first conduit section 19A of the conduit 19, to the second conduit section 19B of the conduit 19. A bypass valve 22 is connected into the bypass conduit 21. Together with the corresponding conduit sections of the conduit 19, the bypass conduit 21 forms a connection path for transporting the gas from the blood reservoir into the air reservoir.

In order to prevent fluid from the blood reservoir getting into the air reservoir, a filter 23 is arranged in the first conduit section 19A of the conduit 19, which filter contains a membrane that is hydrophobic—i.e. permeable for air, but impermeable for fluid. However, since the blood reservoir is filled only up to a maximum fill level, in any case fluid can enter the conduit 19 only in the event of a fault.

For ventilating/venting the closed volume that comprises the blood reservoir and the air reservoir as well as the conduit 19, means 24 are provided for ventilating/venting, which have a ventilating/venting conduit 24A with a ventilating/venting valve 24B, and which are connected to the first conduit section 19A of the conduit 19. The ventilating/venting conduit 24A can in principle lead out from any point of the volume that is to be ventilated/vented. In particular, ventilation/venting should take place in the machine-side part.

Besides the pressure sensor 16 for measuring the pressure in the blood reservoir, a pressure sensor 25 is provided for measuring the pressure in the first conduit section 19A of the conduit 19 between the filter 23 and the compressor 20, and a further pressure sensor 26 is provided for measuring the pressure in the air reservoir 18. At the air reservoir, a temperature sensor T is provided for measuring the temperature of the air that is present in the air reservoir.

The dialysis apparatus has a central control and computing unit 27, which is connected via electrical lines (not shown) to the blood pump 6, the venous hose clamp 12, the bypass valve 22, the ventilation/venting valve 24B, the fill level sensor 15, the compressor 20 and the pressure sensors 16, 25 and 26.

The dialysis apparatus furthermore has an input unit 28, which is connected to the central control and computing unit 27 via a data line 29. The user can enter a volume flow rate for the blood in the venous blood conduit 9 and a maximum permitted value for the return pressure in the venous blood conduit 9 into the input unit, which is designed for example as a keypad. The volume flow rate and/or return pressure can however also be specified by the dialysis apparatus.

In the following, the operation of the dialysis apparatus is described in detail with reference to FIGS. 4 and 5. The central control and computing unit 27 controls the dialysis machine as follows.

At the start of the actual dialysis treatment, the system is initialised with the following process steps.

Figure 4:
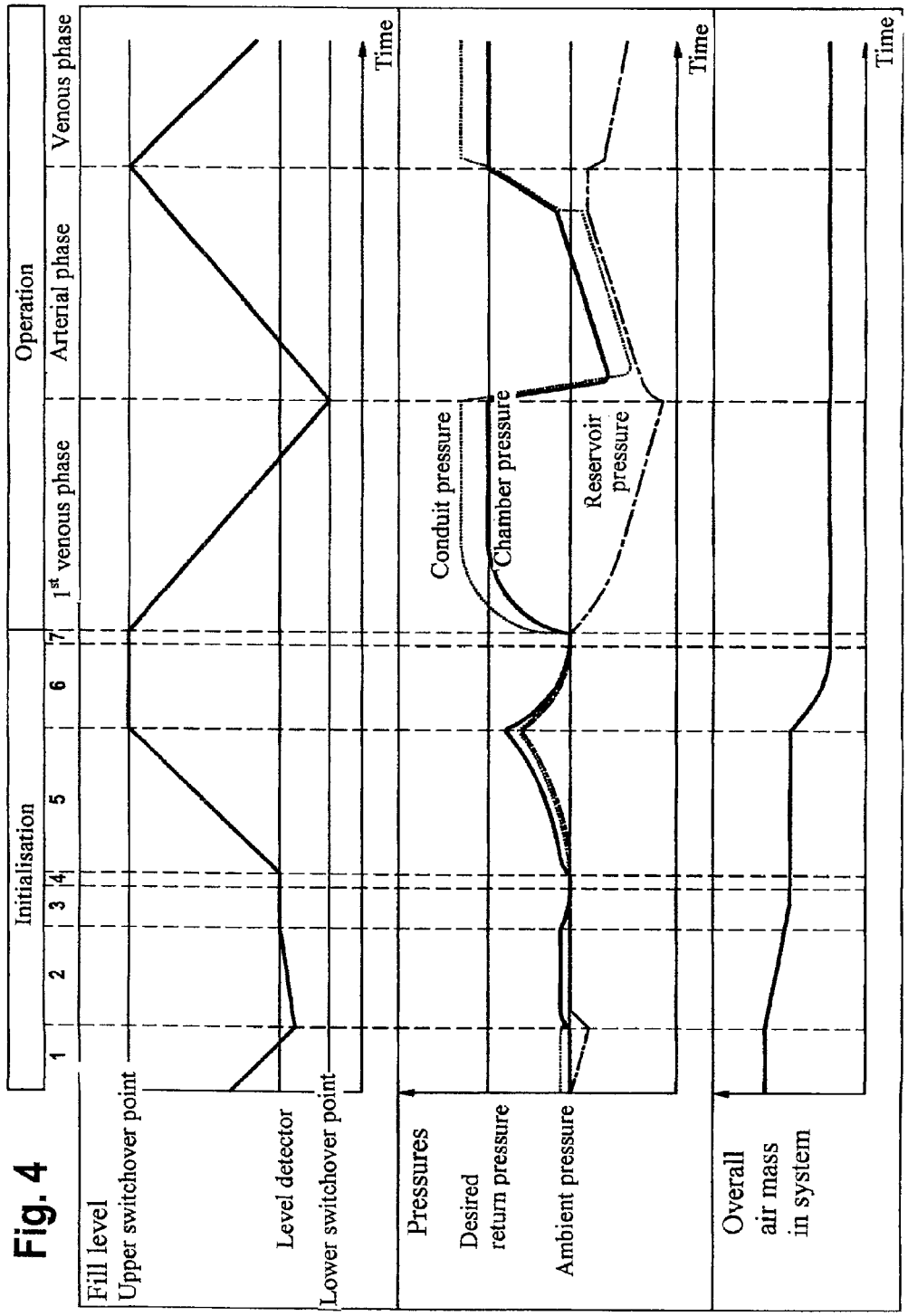
FIG. 4 shows the progression of the fill level and of the pressure during initialization and operation of the blood treatment apparatus of FIG. 3.

FIG. 4 shows the fill level in the blood reservoir as a function of time during the individual phases of initialization. FIG. 4 furthermore shows the progression of the pressure in the blood reservoir, which is described as chamber pressure; of the pressure in the air reservoir, which is described as reservoir pressure; and of the pressure in the first conduit section 19A of the conduit 19, which is described as conduit pressure. FIG. 4 also shows the course over time of the total air mass enclosed in the blood reservoir and in the air reservoir as well as the corresponding sections of conduits 19, 22.

In the first initialization step, the blood level in the blood reservoir is lowered below a certain level that lies between the upper switchover point, at which a switchover is to take place from the arterial phase to the venous phase during operation of the dialysis apparatus, and the lower switchover point, at which a switchover is to take place from the venous phase to the arterial phase. For this, with the blood pump 6 at a standstill, the control and computing unit 27 opens the venous hose clamp 12 and sets the compressor 20 into operation until the desired fluid level has been reached, which is detected by the fill level sensor. FIG. 4 shows that the fill level drops whilst the total air mass in the system remains constant. This step can be skipped if the blood level is already below the desired level.

In the second step, the blood level is then set to the desired level, which is detected by the fill level sensor. For this, the bypass valve 22 and the ventilation/venting valve 24B is opened and the blood pump 6 is operated, with closed venous hose clamp, until the desired level is reached. FIG. 4 shows that the fill level rises to the desired level, whilst the air mass in the system decreases.

Once the desired level is reached, there is a period of waiting until the chamber pressure and reservoir pressure as well as the conduit pressure have adjusted to the ambient pressure. The fill level remains constant here, whilst the air mass decreases further slightly (step 3). Only then is the ventilation/venting valve 24B closed again (step 4).

The blood reservoir is then filled further with blood. With the bypass valve opened, the blood pump 6 is operated until the fill level in the blood reservoir has reached the level of the upper switchover point (step 5). The air mass in the system remains constant here. Since the chamber pressure and the reservoir pressure as well as the conduit pressure are measured with the pressure sensors, the fill level in the blood reservoir can be calculated continuously. The control and computing unit calculates the fill level in the blood reservoir and then halts the blood pump when the fill level has reached the level of the upper switchover point. This will be described in detail later on.

After the control and computing unit has stopped the blood pump 6, the ventilation/venting valve 24B is opened once more, so that the pressure that has built up in the system relaxes to the ambient pressure (step 6). FIG. 4 shows that the fill level remains constant, whilst the chamber pressure and reservoir pressure as well as the conduit pressure drop to the ambient pressure. Since the volume that is enclosed by the system, i.e. the volume of the blood reservoir and the air reservoir as well as the conduits, are known, as are the pressures in the system, the air mass contained in the system can be calculated. This will be described in detail later on.

As the final step in the initialization, the ventilation/venting valve 24B is closed, wherein neither the fill level nor the pressure and the air mass in the system change (step 7). Throughout the entire blood treatment, the ventilation/venting valve remains closed, unless fresh initialization is necessary, for example after an air leak has been detected. The initialization is thus concluded, and the blood treatment starts with the first venous phase.

In the first venous phase, the compressor 20 is operated with a closed bypass valve 22, with the venous hose clamp 12 being open and the blood pump 6 being at a standstill. Whilst the compressor is operating, air from the air reservoir 18 is compressed and supplied to the blood reservoir 11. Through this, the chamber pressure and conduit pressure increase, whilst the reservoir pressure decreases. At the same time, the fill level in the blood reservoir decreases continuously, until the level of the lower switchover point is reached. What is decisive is that the reservoir pressure lies below the chamber pressure, and consequently also below the conduit pressure. An additional aim here is that the reservoir pressure lies below the ambient pressure.

Thereupon the arterial phase begins, in which the blood reservoir is once more filled with the blood taken from the patient, whereupon the venous phase follows on once more, in which the blood from the blood reservoir is supplied back to the patient.

The air reservoir is dimensioned to be large enough that even at the end of the venous phase, there is sufficient air present in the system in order to be able to maintain the desired return pressure in the blood reservoir. In order to be able to set all the operating points with a return pressure from 0 to 500 mmHg relatively at a stroke volume up to 60 ml with the same initialization, in practice an air reservoir with a storage volume of approx. 300 ml is required.

Figure 5:
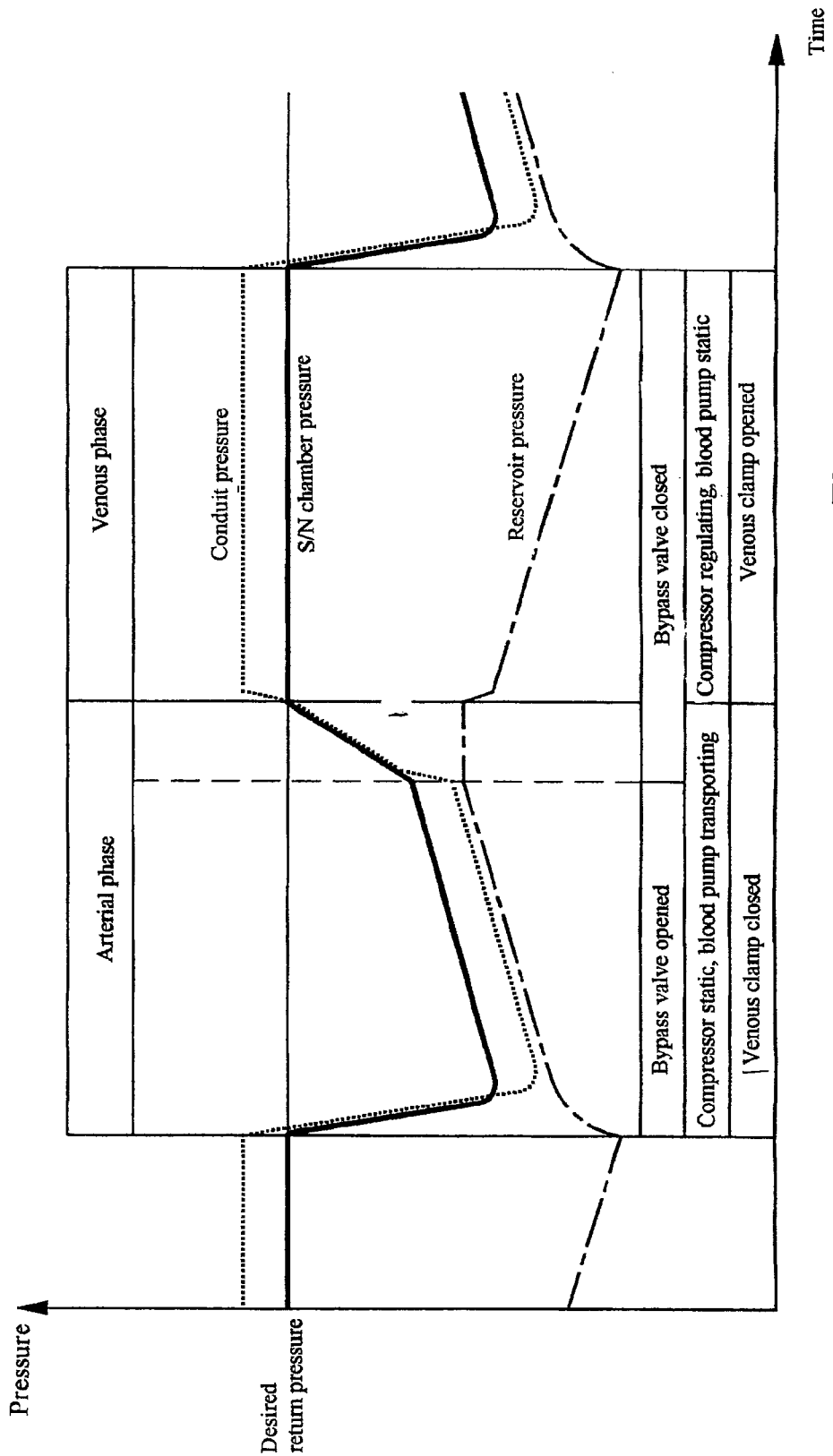
FIG. 5 shows the pressure progression during the arterial and venous phases that follow on from one another during the operation of the blood treatment apparatus of FIG. 3.

The chronological progression of the chamber pressure and reservoir pressure as well as the conduit pressure during the actual arterial and venous phases after the initialization of the system is shown in FIG. 5, which shows an excerpt from FIG. 4.

Throughout the entire arterial phase, the blood pump 6 is operated, while the compressor 20 is at a standstill. The venous hose clamp 12 remains closed throughout the entire arterial phase.

At the start of the arterial phase, the control and computing unit 27 opens the bypass valve 22, so that the air displaced out of the blood reservoir 11 passes via the bypass conduit 21 into the air reservoir 18. Consequently, the reservoir pressure rises, whilst the chamber pressure and the conduit pressure initially drop, and then likewise rise as it were with the reservoir pressure. The air mass contained in the blood reservoir and in the corresponding conduit volume thus decreases continuously.

As soon as the air mass contained in the blood reservoir and the conduit volume has reached a predetermined amount, which results from the desired stroke volume and the desired return pressure, the control and computing unit closes the bypass valve. Consequently, two separate air volumes arise, i.e. the air volume in the blood reservoir with the corresponding conduit sections, and the volume of the air reservoir with the corresponding conduit sections. The blood pump is then operated with closed bypass valve, so that the reservoir pressure remains constant, whilst the air in the blood reservoir and the corresponding conduit volume is compressed until, on reaching the desired stroke volume, the desired return pressure too is reached.

FIG. 5 shows that by the end of the arterial phase, the chamber pressure and conduit pressure have risen to the desired return pressure, whilst the reservoir pressure throughout the entire arterial phase always lies below the chamber pressure and conduit pressure, in particular below the ambient pressure. Through this, it is ensured that even in the event of a fault in the system, for example in the event of a leak in the compressor, air does not get out of the air reservoir into the blood reservoir.

Instead of a division of the arterial phase into a first and a second time interval, other embodiments are also possible. An alternative embodiment provides that in place of the bypass valve 22, a pressure-controlled valve is used, which opens when a limit pressure corresponding to the return pressure is reached, so that in a certain time range a constant pressure prevails in the blood reservoir, through which advantages according to the present invention can also be achieved.

The control and computing unit subsequently switches over to the venous phase, wherein the bypass valve remains closed, the blood pump is at a standstill, and the compressor is set into operation and the venous hose clamp is opened. The compressor is operated throughout the entire venous phase, whilst the blood pump remains at a standstill. During the venous phase, the venous hose clamp remains open and the bypass valve remains closed.

The compressor transports air out of the air reservoir into the blood reservoir in order to build up an overpressure, so that blood is transported out of the blood reservoir. Here, the compressor is operated in such a way that the desired return pressure is achieved in the blood reservoir. Since the blood reservoir is continually supplied with air from the air reservoir, the reservoir pressure continually decreases. Once again, what is decisive is that the reservoir pressure always lies below the chamber pressure and conduit pressure, in particular below the ambient pressure, so that an air infusion from the air reservoir into the patient in the event of a fault is prevented through relaxation of the volume in the air reservoir. The venous phase is then ended when the blood level in the blood reservoir has once again dropped to the level of the lower switchover point. The next arterial phase then follows on.

In the following, the calculation of the blood volume $V_{Blood}$ that is present in the blood reservoir is described, which is undertaken by the control and computing unit during operation of the dialysis apparatus, either continuously or at predetermined intervals. If the blood volume is known, this can be used for comparison with the switchover points from the arterial to the venous phase or vice versa.

To calculate the blood volume $V_{Blood}$ which is present in the blood reservoir and which is to be transported, it is first of all necessary to determine the air mass in the blood reservoir. After pressure equalisation has been carried out, the following applies:

$$pV = \frac{m}{M_m}RT$$

where:
p=pressure (absolute), V=volume, m=mass, $M_m$=molar mass, R=general gas constant, and T=temperature.

Since $M_m$ and R are constant, and no absolute values are required for the air mass, these do not need to be taken into account explicitly. Accordingly, all that needs to be determined is $$\frac{pV}{T} \equiv m.$$

To determine the total air mass, the sum of all partial air masses, i.e. the air mass in the blood reservoir, the corresponding conduits and in the air reservoir, must be formed. For this, all volumes filled with air are multiplied by the respectively prevailing pressure, and divided by the temperature.

$$\left(\frac{pV}{T}\right)_{total} = \frac{p_{blood\ reservoir} \times V_{blood\ reservoir/air}}{T_{blood\ reservoir}} +$$
$$\frac{p_{conduit} \times V_{conduit}}{T_{conduit}} + \frac{p_{air\ reservoir} \times V_{air\ reservoir}}{T_{air\ reservoir}}$$

$$T_{blood\ reservoir} \approx 273.15K + 36K$$

$$T_{conduit} \approx \frac{T_{blood\ reservoir} + T_{air\ reservoir}}{2}$$

The air volume of the blood reservoir $V_{blood\ reservoir/air}$ changes during operation. When the blood level is at the height H of the level detected by the fill level sensor 15, then $$V_{blood\ reservoir/air} = V_{blood\ reservoir/air\ UT} - \Delta V_{blood\ reservoir/UT-H}$$

where $V_{blood\ reservoir/air\ UT}$ is the air volume in the blood reservoir at the lower switchover point UT and $\Delta V_{blood\ reservoir/UT-H}$ is the volume difference between the lower switchover point UT and the height of the fill level in the blood reservoir detected by the fill level sensor 15.

At the end of the initialization at the upper switchover point OT, there is additional blood with the total stroke volume $V_{stroke}$ located in the blood reservoir, so that $V_{blood\ reservoir/air} = V_{blood\ reservoir/air\ UT} - V_{stroke}$.

The remaining volumes remain constant. Here, the temperatures can be set as constant as a good approximation, if no temperature compensation is carried out. Preferably however, a temperature sensor for temperature measurement is provided at least in the air reservoir, so that temperature compensation can be carried out. Temperature sensors can however also be provided for the other pressure values.

The transported blood volume $V_{blood}$ in the blood reservoir is calculated throughout the entire cycle at every program loop. Here, the air volume $V_{blood\ reservoir/air}$ that is enclosed in the blood reservoir is calculated on the basis of the pressures measured, and the difference from the air volume in the blood reservoir at the lower switchover point UT and the air volume of the blood reservoir is formed.

$$V_{blood\ reservoir/air} = \frac{\left(\frac{pV}{T}\right)_{total} - \frac{p_{conduit} V_{conduit}}{T_{conduit}} - \frac{p_{air\ reservoir} V_{air\ reservoir}}{T_{air\ reservoir}}}{\frac{p_{blood\ reservoir}}{T_{blood\ reservoir}}}$$

$$V_{blood} = V_{blood\ reservoir/air\ UT} - V_{blood\ reservoir/air}$$

The total air mass $(pV/T)_{total}$ remains unchanged after initialization of the system, since the venting valve remains closed. Since the calculation of the blood volume $V_{blood}$ takes place with a running blood pump or running compressor, a smoothing of the pressure signals and of the calculated blood volume $V_{blood}$ is carried out.

The switchover from the arterial to the venous phase (OT) takes place when the difference from the calculated blood volume $V_{blood}$ and the set stroke volume $V_{stroke}$ is equal to zero, and the switchover from the venous to the arterial phase takes place when the calculated blood volume is equal to zero.

In the following, it is described how the control and computing unit calculates the point in time at which within the arterial phase there is a switchover between the first and the second time interval of the arterial phase.

As has already been described above, the switchover point from the arterial to the venous phase and back is possible through a simple comparison of the blood volume with the stroke volume or zero. As mentioned above, the arterial phase is divided into a first and a second time interval. In the first arterial phase, the blood pump transports blood via the dialyser, with open bypass valve, into the blood reservoir. Through this, the low pressure, which has previously built up in the air reservoir in the venous phase, is used to support the pump. In the second arterial phase, the air reservoir is decoupled from the rest of the system by closing the bypass valve, and the pressure in the blood reservoir rises markedly through the transported blood volume. At the end of the second arterial phase, the desired return pressure or reference pressure should prevail in the blood reservoir. The switchover point between the first and second arterial phase must therefore be selected such that the still outstanding volume of blood builds up the reference pressure in the blood reservoir and the conduit by the time of the upper switchover point OT.

Accordingly, what must be calculated is the air mass which, during compression to the air volume available at the upper switchover point in the blood reservoir and the conduit, builds up the reference pressure $p_{reference}$. The air mass in the blood reservoir and the conduit is $$\frac{p_{blood\ reservor} V_{blood\ reservoir}}{T_{blood\ reservoir}} + \frac{p_{conduit} V_{conduit}}{T_{conduit}} = \left(\frac{pV}{T}\right)_{total} - \frac{p_{air\ reservoir} V_{air\ resrevoir}}{T_{air\ reservoir}}.$$

At the switchover point from the first to the second time interval of the arterial phase, the air mass that is present in the blood reservoir and the conduit must be equal to the air mass that is present at the upper switchover point OT in the blood reservoir and the conduit.

$$\left(\frac{pV}{T}\right)_{total} - \frac{p_{air\ reservoir} V_{air\ reservoir}}{T_{air\ reservoir}} = \frac{p_{ref} \cdot V_{blood\ reservoir/air\ OT}}{T_{blood\ reservoir}} + \frac{p_{reference} V_{conduit}}{T_{conduit}}$$

Here, $V_{blood\ reservoir/air\ OT}$ is the air volume in the blood reservoir at the upper switchover point OT.

During the arterial phase, the control and computing unit checks whether the upper equation is fulfilled. As soon as the equation is fulfilled, the second time interval of the arterial phase begins, wherein the bypass valve is closed. The blood pump is operated by the control and computing unit in the second interval at the same transportation rate, until the desired stroke volume and thus the upper switchover point OT is reached.

A leak in the closed volume can result in a change in the amount of gas enclosed in the system. If the leak lies in the overpressure range of the system, i.e. in the region of the blood reservoir or the adjacent conduit sections, then the leak leads to a reduction in the enclosed amount of air, through which the fill level of blood in the blood reservoir rises. There is a danger here of the blood reservoir filling up and the blood level rising up to the hydrophobic membrane, so that the arterial phase can no longer be ended properly. Conversely, in the case of a leak in the low pressure range, i.e. in the gas reservoir or through ingress of air from the blood system, the enclosed amount of air is increased, so that the fill level of the blood in the blood reservoir drops. This can lead to the situation where the blood level drops too quickly in the venous phase, which can lead to unwanted foam formation, and in extreme cases even to an air alarm. However, this can be monitored in that the amount of air enclosed in the system is monitored. Such monitoring of the quantity of air can be provided in the apparatus according to the present invention.

Monitoring of the quantity of air to detect a leak is carried out in that the point in time is recorded at which the fill level sensor 15 detects the fill level in the blood reservoir 11, i.e. the blood reaches the predetermined level. Thus for this point in time, the actual fill level of the blood is known. This value is compared with the fill level calculated from the pressure values at this point in time. If the difference between the measured and the calculated fill levels is greater than a predetermined limit value, then the quantity of air enclosed in the system has changed significantly, which can be attributed to a leak in the system. In this case, the system is initialised afresh. If the fault occurs too frequently, the central control and computing unit 27 breaks off the treatment.

An alternative evaluation is based not on the measured and calculated fill levels, but on comparing the point in time at which the fill level sensor 15 detects the specified fill level with the calculated point in time at which the specified fill level should be achieved. If there is a significant difference, it is concluded that there is a leak in the system.

Another embodiment additionally detects a leak in the system in the part which faces away from the blood reservoir, and which is behind the filter 23, after the rise in the fill level over the level detected by the fill level sensor in the arterial phase in that with the pressure sensor 16 in the blood reservoir 11, a pressure that rises too markedly is detected, wherein the pressure and/or the pressure rise per unit time exceeds a predetermined limit value. In this case, the blood reaching the filter leads to an increase in pressure, which drastically reduces the compliance in this part of the system. This applies in particular to the case in which a pressure sensor is used which measures the pressure in direct contact, i.e. without a compressible intermediate space.

Figure 6:
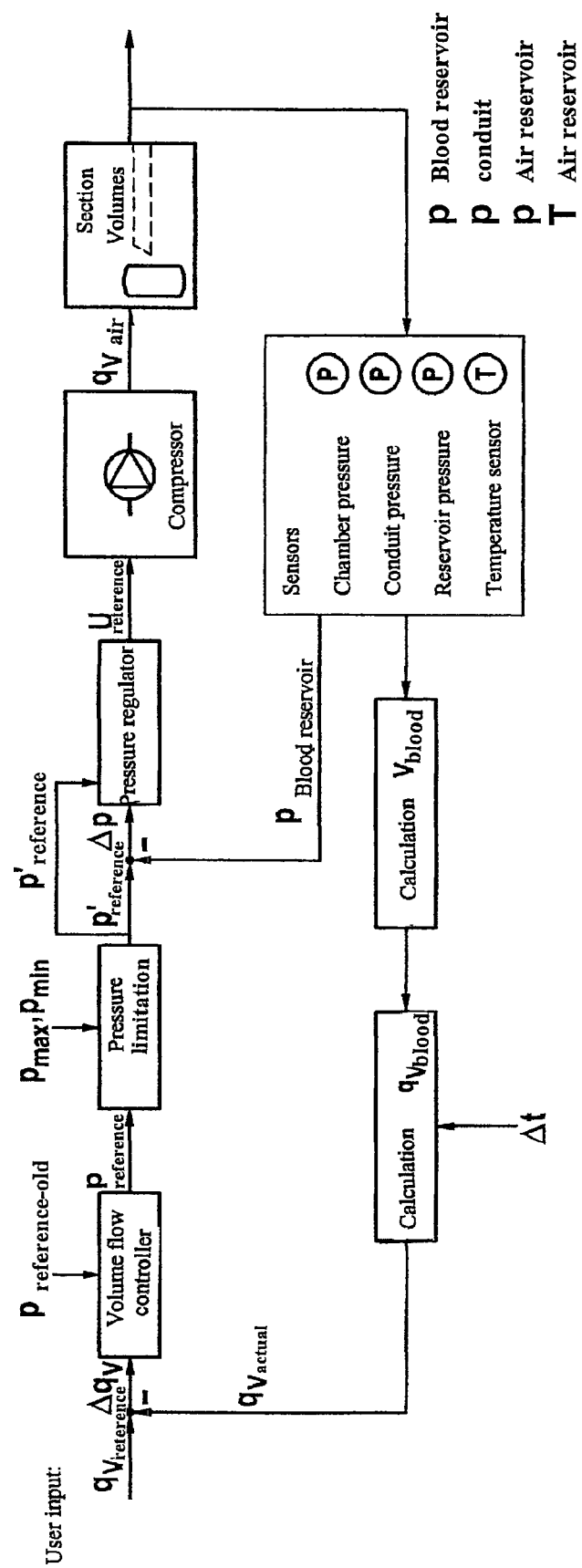
FIG. 6 shows a block diagram of the control device according to the present invention, of the blood treatment apparatus according to the present invention, of FIG. 3.
Figure 7:
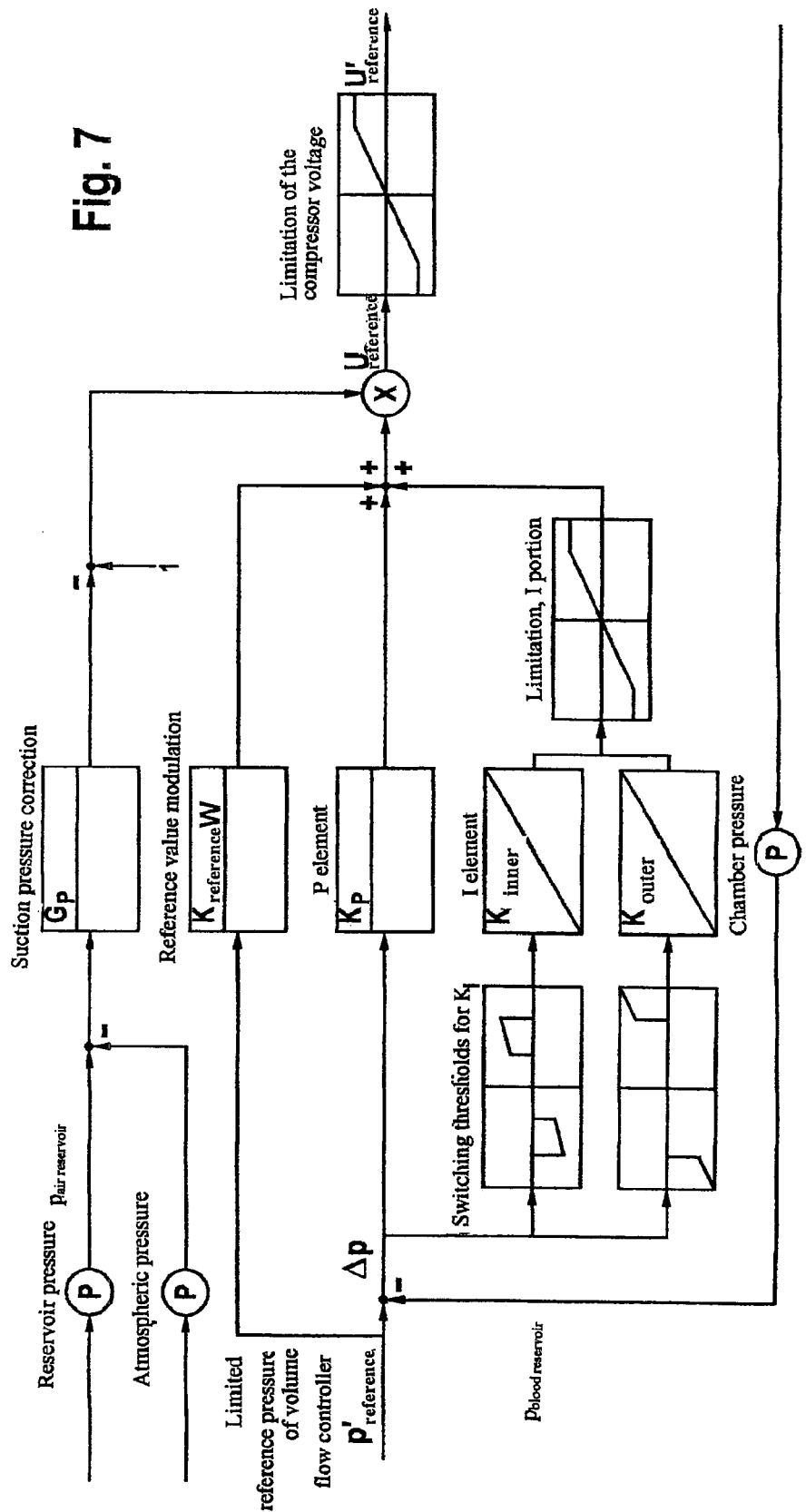
FIG. 7 shows a block diagram of the pressure regulator of the control device of FIG. 6.

In the following, the control device according to the present invention for the dialysis apparatus is described in detail, with reference to FIGS. 6 and 7, which is a constituent part of the dialysis apparatus that is described with reference to FIGS. 3 to 5. Here, the control device makes use of the components that are already present in a dialysis apparatus. The control device is part of the central computing and control unit 27 of the dialysis apparatus. Implemented in the central computing and control unit is the controller structure shown in the block diagrams of FIGS. 6 and 7, whose structure and function is as follows.

The controller structure provides for both control of the volume flow rate and of the pressure in the venous blood conduit 9. At the start of the regular venous phase, i.e. not immediately after initialization of the system (FIG. 3), the blood reservoir 11 is already subjected to pressure. The blood reservoir 11 is pre-pressurerized with the reference pressure at the end of the last arterial phase. Through this, it is achieved that immediately after opening the venous hose clamp 12, the blood from the blood reservoir 11 can be supplied back to the patient.

Regulation takes place in individual cycles with a predetermined loop duration, with typical values for the loop duration being for example 50 msec. First of all, the reference value for the volume flow rate $q_{Vreference}$ is compared with the actual volume flow rate $q_{Vactual}$ at the start of the venous phase. For this the actual volume flow rate $q_{Vactual}$ is calculated. The following applies:

$$\Delta q_V = q_{Vreference} - q_{Vactual}$$

Regulation is based on the fact that with an external controller, the pressure in the blood reservoir 11 is determined, at which the given volume flow rate is achieved in the venous blood conduit 9, wherein with an internal controller, the means for compressing gas 20, for example the compressor, are operated in such a way that the established reference pressure $p_{reference}$ actually is achieved in the blood chamber 11.

In the case of the reference pressures or limit pressures that are to be achieved with the internal and external controller, these are preferably relative pressures $\Delta p$ in relation to the ambient pressure. For preference, a displacement of the zero point of the relative limit pressures or reference pressures due to changes in the ambient pressure is recorded. For this, in the case of a preferred embodiment, a pressure sensor is provided which measures the ambient pressure.

The actual volume flow $q_{Vactual}$ is determined from the quotient of the blood volume $\Delta V_{blood}$, which has changed compared with the preceding program loop, and the loop duration $\Delta t$, with the blood volume for a loop being calculated as described above from the respective chamber pressure, conduit pressure and reservoir pressure, possibly with temperature compensation.

The volume flow regulator must at all events be slower than the pressure regulator for adjusting the pressure, since otherwise the reference pressure in the blood reservoir 11 is varied too quickly. The volume flow regulator is preferably an integral controller.

The algorithm uses the reference pressure of the last loop run and adds on the deviation $\Delta q_V$ multiplied by a factor $K_{qV}$.

$$p_{reference} = p_{reference\_old} + K_{qV} \times \Delta q_V$$

In the first venous phase after initialization of the system, the factor $K_{qv}$ is chosen to be smaller and the first reference pressure $p_{reference\_old}$ is chosen with $p_{atmos}+50$ hPa. This ensures that the blood flow is slowly increased to the desired blood flow, so that pressure peaks cannot occur. The control algorithm for the pressure is also chosen to be slower in the first loop run.

Following on from the determination of the reference pressure $p_{reference}$, the established reference pressure is limited by a pressure limitation. For one thing, the pressure limitation ensures that the pressure that is to be adjusted is not greater than the specified maximum tolerable return pressure $p_{max}$, i.e. that the pressure that is to be adjusted does not exceed the physiological limits. For another, the pressure limitation ensures that the pressure that is to be adjusted does not drop below a minimum pressure, in this case the atmospheric pressure $p_{min}$. The upper limit value for the pressure $p_{max}$ can lie above the limit value at which the alarm devices that are present in known dialysis apparatuses trigger an alarm, so that it can be ensured that for example when a patient connection point is blocked, a pressure alarm is triggered, but that the cycle is not stopped without triggering an alarm.

The reference pressure that is calculated and limited by the volume flow regulator is then adjusted by the pressure regulator. The pressure regulator is preferably a PI controller with a connected integrator. FIG. 7 shows the block diagram of the pressure regulator, wherein FIG. 7 is to be understood as an excerpt from FIG. 6. The pressure regulator produces a control voltage $U_{reference}$ or $U'_{reference}$, with which the compressor 20 is operated, wherein the rotational speed (output) of the compressor rises with increasing control voltage.

The pressure regulator provides for a suction pressure correction, in which depending on the difference between the pressure in the air reservoir 18 and the atmospheric pressure, i.e. the relative pressure, the output signal of the regulator is increased. Since the compressor 20 creates a low pressure in the air reservoir 18, during the venous phase the compressor must work increasingly against the pressure difference that arises, so that less air is transported at the same speed. With the suction pressure correction, it is ensured that the control voltage is raised accordingly, in order to compensate the suction pressure drop with increasing low pressure in the air reservoir.

The integrator of the pressure regulator has two switching thresholds ($\Delta p_{inner}$ and $\Delta p_{outer}$). In the event of reference value deviations that are too high (outer threshold), the I proportion is reduced, in order to avoid overshooting. If however there is only a very small deviation (inner threshold), the I proportion can be set to zero. The I-proportion is calculated as follows, taking account of relative values for the pressure in relation to the ambient pressure:

$$I_{new} = I_{old} + \Delta p \times K_I$$

$$K_I = K_{I\_outer} \text{ if } \Delta p > \Delta p_{outer}$$

$$K_i := K_{I\_inner} \text{ if } \Delta p_{inner} < \Delta p < \Delta p_{outer}$$

$$K_i = 0 \text{ if } \Delta p < \Delta p_{inner}$$

The maximum I proportion is limited, in order to prevent too great a deviation. The controller output is calculated from the sum of the P and I proportion with the reference value modulation:

$$S_{controller} = \Delta p \times K_p + I_{new} + p'_{reference} \times K_{referenceV}$$

The controller output is subsequently, as described above, supported by the suction pressure correction depending on the absolute pressure in the air reservoir 18:

$$S_{output} = S_{controller} \times (1 - (G_p \times (p_{air\ reservoir} - p_{atmos})))$$

Since the compressor 20 can be operated only with a maximum operating voltage, the control voltage $U_{reference}$ is limited to the maximum and minimum control voltage. The compressor is operated with the control voltage $U'_{reference}$.

It must be noted that both the reference pressure and the integrator of the pressure regulator from the preceding program loop or the preceding cycles is required. Moreover, the reference pressure is needed for determining the switchover point from the first to the second time interval of the arterial phase. For this reason, the two values are stored for the interim.

The invention claimed is:

1. An extracorporeal blood treatment apparatus comprising:
   a device for transporting blood in a blood conduit of an extracorporeal blood circuit that has an arterial blood conduit leading to a blood treatment unit and a venous blood conduit leading away from the blood treatment unit;
   means for collecting blood that has a specified closed volume, said means for collecting blood being located in the venous blood conduit, and,
   an apparatus for controlling the device for transporting blood, said apparatus for controlling the device for transporting blood comprising:
   means for setting a particular volume flow for the blood flowing in the blood conduit;
   means for producing a control signal for the device for transporting blood in the blood conduit, wherein the control signal is dimensioned such that the blood in the blood conduit is transported at the specified volume flow rate;
   means for setting at least one particular pressure limit value for the blood conduit;
   means for measuring the pressure in the blood conduit; and
   means for comparing the pressure in the blood conduit with the at least one specified pressure limit value,
   wherein the means for producing a control signal is configured such that the control signal is produced when the specified pressure limit value in the blood conduit is reached, wherein the control signal is dimensioned such that when the blood is transported in the blood conduit, a pressure is established that conforms to the at least one pressure limit value,
   wherein the blood treatment apparatus is designed as a blood treatment apparatus for operation with one patient connection point,
   wherein the arterial blood conduit and the venous blood conduit have a common patient connection point,
   wherein the device for transporting blood is a device for producing a specified pressure in the means for collecting blood, such that blood that has collected in the means for collecting blood can be displaced from the means for collecting blood, the device for transporting blood further comprising:
   means for storing air which has a closed volume, and
   means for compressing air, which is in flow connection, via a connection path, with the means for storing air and the means for collecting blood,
   wherein air from the means for storing air can be conveyed into the means for collecting blood, thereby displacing the blood that has collected in the means for collecting blood, and
   wherein the means for producing a control signal comprises:
   a first control circuit comprising means for calculating a reference pressure for the closed volume of the means for collecting blood, which is dimensioned such that the specified volume flow rate is achieved in the venous blood conduit, and
   a second control circuit comprising a control signal for the means for compressing air, which is dimensioned such that the calculated reference pressure is achieved in the closed volume of the means for collecting blood, at which the specified volume flow rate is achieved in the venous blood conduit.

2. The extracorporeal blood treatment apparatus of claim 1, wherein the first control circuit further comprises means for limiting the reference pressure to a predetermined limit value.

3. The extracorporeal blood treatment apparatus of claim 1, wherein the first control circuit comprises an integral controller that determines the reference pressure through temporal integration of the difference between the specified volume flow and the actual volume flow.

4. The extracorporeal blood treatment apparatus of claim 1, wherein the second control circuit comprises a PI control unit.

5. The extracorporeal blood treatment apparatus of claim 1, wherein the second control circuit further comprises means for compensating that are configured such that the control signal for the means for compressing air is altered based on the pressure in the closed volume of the means for storing air.

6. An extracorporeal blood treatment apparatus comprising:
   a device for transporting blood in a blood conduit of an extracorporeal blood circuit that has an arterial blood conduit leading to a blood treatment unit and a venous blood conduit leading away from the blood treatment unit;
   means for collecting blood that has a specified closed volume, said means for collecting blood being located in the venous blood conduit, and,
   an apparatus for controlling the device for transporting blood, said apparatus for controlling the device for transporting blood comprising:
   means for setting a particular volume flow for the blood flowing in the blood conduit;
   means for producing a control signal for the device for transporting blood in the blood conduit, wherein the control signal is dimensioned such that the blood in the blood conduit is transported at the specified volume flow rate;

means for setting at least one particular pressure limit value for the blood conduit;

means for measuring the pressure in the blood conduit; and means for comparing the pressure in the blood conduit with the at least one specified pressure limit value, wherein the means for producing a control signal is configured such that the control signal is produced when the specified pressure limit value in the blood conduit is reached, wherein the control signal is dimensioned such that when the blood is transported in the blood conduit, a pressure is established that conforms to the at least one pressure limit value, wherein the blood treatment apparatus is designed as a blood treatment apparatus for operation with one patient connection point, wherein the arterial blood conduit and the venous blood conduit have a common patient connection point, wherein the device for transporting blood is a device for producing a specified pressure in the means for collecting blood, such that blood that has collected in the means for collecting blood can be displaced from the means for collecting blood, the device for transporting blood further comprising:

means for storing air which has a closed volume, and means for compressing air, which is in flow connection, via a connection path, with the means for storing air and the means for collecting blood, wherein air from the means for storing air can be conveyed into the means for collecting blood, thereby displacing the blood that has collected in the means for collecting blood, and wherein the means for producing a control signal further comprises:

means for determining the volume of blood enclosed in a closed volume, and means for calculating the decrease in the closed blood volume in a given time interval.

7. The extracorporeal blood treatment apparatus of claim 6, wherein the means for determining the blood volume comprises:

means for measuring the pressure in the closed volume of the means for collecting blood, means for measuring the pressure in the closed volume of the means for storing air, means for measuring the pressure in a closed volume of the connection path between the means for collecting blood and the means for compressing air, and wherein the means for determining the volume of blood are configured such that the blood volume is calculated based on the measured pressure in the closed volume of the means for collecting blood, the closed volume of the means for storing air, and the closed volume of the connection path between the means for collecting blood and the means for compressing air.

8. A method for transporting blood in a blood conduit of an extracorporeal blood circuit of an extracorporeal blood treatment apparatus comprising:

specifying a particular volume flow rate for the blood flowing in the blood conduit;

specifying at least one particular pressure limit value in the blood conduit;

determining the pressure in the blood conduit;

comparing the pressure in the blood conduit with the at least one specified limit value for the pressure in the blood conduit; and transporting the blood in the blood conduit at the specified volume flow rate where the amount of pressure in the blood conduit lies below the at least one pressure limit value, controlling the pressure in the blood conduit so that a pressure that conforms to the at least one pressure limit value is achieved in the blood conduit, wherein the circuit has an arterial blood conduit leading to a blood treatment unit and a venous blood conduit leading away from the blood treatment unit, wherein the blood treatment apparatus is designed as a blood treatment apparatus for operation with one patient connection point, wherein the arterial blood conduit and the venous blood conduit have a common patient connection point, wherein during an arterial phase, blood is transported to the means for collecting blood, said means for collecting blood having a closed volume, wherein during a venous phase, a specified pressure is built up in the means for collecting blood, so that blood that has collected in the means for collecting blood is displaced out of the means for collecting blood, wherein there is continual switching over between the arterial phase and the venous phase, wherein during the venous phase, air is transported to the means for collecting blood with a means for compressing air, and wherein the means for compressing air are controlled such that in the closed volume of the means for collecting blood, a pressure is achieved such that the blood in the blood conduit is transported at the specified volume flow rate when the amount of pressure in the blood conduit lies below the limit value, and such that when the specified limit value for the pressure in the blood conduit is reached, a pressure is brought about which conforms to the limit value.

9. The method of claim 8, wherein during the venous phase, air is transported from the means for storing air to the means for collecting blood with the means for compressing air, said means for compressing air being arranged in a connection path between the means for collecting blood and the means for storing air.

10. The method of claim 8, wherein a reference pressure is calculated for the closed volume of the means for collecting blood, such that the specified volume flow rate is achieved in the venous blood conduit, and that the means for compressing air is actuated such that in the closed volume of the means for collecting blood, the calculated reference pressure is achieved at which the specified volume flow rate is achieved in the venous blood conduit.

11. The method of claim 10, wherein the calculated reference pressure is limited to a specified limit value.

12. The method of claim 8, wherein the means for compressing air are controlled depending on the pressure in the closed volume of the means for storing air.

13. The method of claim 8, further comprising:

calculating the actual volume flow rate in the venous blood conduit in that the blood volume in a closed volume is determined, and the decrease in the blood volume that is enclosed in the closed volume in a given time interval is calculated.

14. The method of claim 13, further comprising:

measuring the pressure in the closed volume of the means for collecting blood, the pressure in the closed volume of the connection path between the means for collecting blood and the means for compressing air, and the pressure in the closed volume of the means for storing air to determine the blood volume; and calculating the blood volume based on the measured pressure in the closed volume of the means for collecting blood, in the closed volume of the connecting path between the means for collecting blood and the means for compressing air, and in the closed volume of the means for storing air.

\* \* \* \* \*

UNITED STATES PATENT AND TRADEMARK OFFICE
CERTIFICATE OF CORRECTION

PATENT NO.        : 8,632,487 B2                                        Page 1 of 1
APPLICATION NO. : 12/602813
DATED             : January 21, 2014
INVENTOR(S)       : Günther et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this
Twenty-second Day of September, 2015

Michelle K. Lee
*Director of the United States Patent and Trademark Office*